US008754125B2

(12) United States Patent
Ding et al.

(10) Patent No.: US 8,754,125 B2
(45) Date of Patent: Jun. 17, 2014

(54) ANTIMICROBIAL PRESERVATION OF PROPOFOL EMULSIONS

(75) Inventors: Min Ding, Tarrytown, NY (US); Rajeshwar Motheram, Dayton, NJ (US); Glenn Sblendorio, Mahwah, NJ (US)

(73) Assignee: The Medicines Company, Parsippany, NJ (US)

( * ) Notice: Subject to any disclaimer, the term of this patent is extended or adjusted under 35 U.S.C. 154(b) by 0 days.

(21) Appl. No.: 13/252,667

(22) Filed: Oct. 4, 2011

(65) Prior Publication Data

US 2012/0149770 A1 Jun. 14, 2012

Related U.S. Application Data

(60) Provisional application No. 61/390,010, filed on Oct. 5, 2010.

(51) Int. Cl.
*A61K 31/235* (2006.01)
*A61K 31/05* (2006.01)

(52) U.S. Cl.
USPC .......................................... 514/543; 514/731

(58) Field of Classification Search
None
See application file for complete search history.

(56) References Cited

U.S. PATENT DOCUMENTS

| 6,534,547 | B1 * | 3/2003 | Carpenter ..................... 514/731 |
| 6,579,469 | B1 * | 6/2003 | Hedgpeth et al. ........ 252/182.11 |
| 2002/0022667 | A1 * | 2/2002 | Pace et al. ..................... 514/731 |
| 2004/0171691 | A1 | 9/2004 | Tang et al. |
| 2005/0004234 | A1 | 1/2005 | Bell et al. |
| 2005/0027019 | A1 | 2/2005 | Zhang et al. |

FOREIGN PATENT DOCUMENTS

| WO | 00/21517 | 4/2000 |
| WO | 00/24376 | 5/2000 |
| WO | 01/97779 | 12/2001 |

OTHER PUBLICATIONS

International Search Report for PCT/US2011/054744, dated Apr. 10, 2012.
Extended European Search Report, dated Feb. 14, 2014, issued in corresponding European Application No. 11831439.2.

* cited by examiner

*Primary Examiner* — Dennis Heyer
(74) *Attorney, Agent, or Firm* — Roylance, Abrams, Berdo & Goodman, LLP

(57) ABSTRACT

The invention provides intravenous formulations of propofol in an oil-in-water emulsion, having a combination of preservatives.

16 Claims, No Drawings

ANTIMICROBIAL PRESERVATION OF PROPOFOL EMULSIONS

FIELD OF THE INVENTION

The invention relates generally to the field of pharmaceutical preservatives, and more specifically to preservatives for intravenous formulations.

BACKGROUND OF THE INVENTION

Propofol (2,6-diisopropylphenol) is an injectable anesthetic widely used in veterinary and human medicine. Propofol has the useful attributes of rapid onset, rapid recovery, and safety in prolonged use. It has proven to be particularly suitable for maintaining long-term sedation to hospital patients in intensive care units. (I. Smith et al., *Anesthesiology*, 1994, 81:1005-1043.) Administration of drugs to sedated patients in a hospital setting is preferably accomplished via a parenteral route, most preferably via intravenous administration.

Propofol is a water-insoluble oil, and in order to prepare a pharmaceutically acceptable formulations suitable for parenteral administration, the active pharmaceutical ingredient must be dispersed or suspended in an isotonic, buffered, nontoxic aqueous phase. For convenience, and to reduce the opportunities for error and infection, it is preferable that the suspension or dispersion be pre-formed and immediately available for routine administration by hospital staff. This requires the formulation to be stable to storage, and it is desirable that there be no requirement for refrigerated or temperature-controlled storage.

A relatively small number of stable parental propofol formulations have been developed. A stabilized oil-free emulsion of propofol in water has been described (U.S. Pat. No. 5,637,625), but such a composition seems likely to be extremely irritating upon intravenous administration, and has not achieved commercial acceptance. Suspensions and dispersions based on a variety of synthetic carriers and amphiphilic excipients have been described (e.g., U.S. Pat. Nos. 4,056,635, 4,452,817, 6,150,423, 6,534,547, 7,034,013, 7,326,735 and 7,550,155), but synthetic carriers and excipients tend to be irritating and/or toxic at the high blood levels reached with continuous administration.

The commercially available product, marketed under the trade name DIPRIVAN™, is a less-irritating and non-toxic oil-in-water emulsion comprising 10% soy bean oil dispersed in water, with egg lecithin as a stabilizing surfactant. Propofol is present at 1% or 2% by weight, dissolved in the oil phase. Glycerol is present at about 2.25% to render the suspension isotonic. The amount of oil used presumably strikes a balance between the level of pain or irritation at the injection site, which is reduced as the propofol is diluted, and the hyperlipidemia that may result from prolonged administration of triglyceride emulsions.

Parenteral oil-in-water emulsions such as DIPRIVAN™ are based on naturally-occurring vegetable oils that are amenable to metabolism by the human body. While this is advantageous from the toxicologist's point of view, it presents a problem in that naturally-occurring triglycerides are also a ready source of metabolic energy for bacteria and fungi. A 10% isotonic emulsion of such an oil is a particularly hospitable and energy-rich environment, and accidental contamination with microorganisms, for example by insertion of a non-sterile needle into a vial of such an emulsion, is therefore likely to result in rapid microbial growth. A subsequent withdrawal of another dose from the vial can then lead to the introduction of pathogens into the bloodstream of a hospitalized patient, with dire consequences. (See: R. Nichols, J. Smith, *New Engl. J. Med.*, 1995, 333:184-185; M. Sosis et al., *Anesth. Anal.*, 1995, 81:132-134; J. Crowther et al., *Anesth. Anal.*, 1996, 82:475-478; see also references therein.) For this reason, the recommended procedure in hospitals is to discard partially-used vials of DIPRIVAN™, which leads to considerable waste and potentially avoidable expense. Also, to avoid microbial contamination, intravenous ports used for DIPRIVAN™ administration should not be accessed for any other purpose, leading to the expense and risk of complications associated with additional ports and/or intravenous lines.

It would be desirable to avoid such waste, and increase safety, by effectively preventing microbial growth in propofol oil-in-water emulsions. The obvious remedy is the addition of antimicrobial preservatives, but the selection of preservatives suitable for use in oil-in-water emulsions of propofol is surprisingly limited. The chief problems are that the preservative must remain in the aqueous phase to be effective, and it must not destabilize the emulsion. It also must be pharmaceutically acceptable for intravenous administration at its antimicrobially-effective concentration; this is a particular challenge for a drug such as propofol which may be continuously administered over a period of days or weeks.

One class of suitable preservatives known in the art is chelating agents, such as EDTA (U.S. Pat. Nos. 5,714,520, 5,731,356, and 5,908,869) and DTPA (U.S. Pat. No. 6,028, 108), which presumably operate by sequestering polyvalent metal ions (chiefly calcium, magnesium, and zinc) that are essential to the biochemical processes of bacteria and fungi. Unfortunately, such agents also sequester the same metal ions from the patient's bloodstream, and patients receiving high amounts of chelators require constant monitoring of plasma levels of at least zinc. Furthermore, at pharmaceutically acceptable levels, these agents slow, but do not prevent, microbial growth, and the compositions do not meet the criteria of the USP 51 Antimicrobial Preservative Effectiveness Test for Category I products.

Other preservatives that have been identified as potentially of use in soybean oil emulsions include sulfite and metabisulfite salts (U.S. Pat. Nos. 6,147,122 and 6,469,069); benzyl alcohol; benzethonium chloride, EDTA/benzyl alcohol, and sodium benzoate/benzyl alcohol (U.S. Pat. Nos. 6,140,373 and 6,140,374). Benzyl alcohol is used in some generic propofol emulsions. Although sulfite is associated with allergic reactions in some patients, generic propofol emulsions preserved with sulfite are also being marketed. None of these products are considered "antimicrobially preserved" under the USP 51 standard.

Low-oil formulations have been described (e.g., U.S. Pat. Nos. 6,100,302 and 7,097,849), but such compositions only marginally reduce microbial growth. An oil-in-water propofol emulsion featuring a combination of low oil and low pH (U.S. Pat. No. 6,399,087) has been reported to be bacteriostatic. (It is also asserted in U.S. Pat. No. 6,726,919 that there is synergy between propofol itself and a wide range of antimicrobial preservatives, but no evidence in support of such an effect was presented.)

There remains a need for oil-in-water propofol emulsions that are protected against the growth of microbial contaminants.

BRIEF DESCRIPTION OF THE INVENTION

The invention provides pharmaceutical compositions comprising propofol in a sterile oil-in-water emulsion suitable for intravenous administration, which further comprise a combination of antimicrobial agents. In different embodiments of the invention, the combination of antimicrobial agents comprises methyl paraben and 4-chlorobutanol, methyl paraben and benzyl alcohol, or benzyl alcohol and 4-chlorobutanol.

The emulsion preferably comprises propofol in an amount from about 1% to about 8% by weight of the emulsion, a pharmaceutically acceptable propofol-dissolving oil in an amount from about 3% to about 20% by weight of the emulsion, and a pharmaceutically acceptable surfactant in an amount sufficient to stabilize the emulsion, wherein the ratio of oil to propofol is in the range of about 20:1 to about 1:1 by weight. The combination of antimicrobial agents is preferably present in an amount sufficient to suppress the growth of microbial contaminants over a period of 24 hours at 20-25° C.

DETAILED DESCRIPTION OF THE INVENTION

As noted above, there is a need for injectable propofol compositions that are safe, non-irritating, and resistant to microbial growth in the event of accidental contamination. In the course of a screening program intended to identify synergistic combinations of antimicrobial preservatives, the present inventors have discovered that combinations of benzyl alcohol with either 4-chlorobutanol or methyl paraben are effective antimicrobial preservatives for propofol emulsions. The present inventors have also discovered that a combination of methyparaben and 4-chlorobutanol is particularly effective, even at low concentrations where neither preservative is as effective in combination with any other preservative.

Accordingly, the present invention provides injectable pharmaceutical compositions comprising propofol in a sterile oil-in-water emulsion, suitable for intravenous administration, which contain as a preservative a combination of methyl paraben and 4-chlorobutanol, methyl paraben and benzyl alcohol, or benzyl alcohol and 4-chlorobutanol. The benzyl alcohol, methyl paraben and 4-chlorobutanol are each independently present at a concentration of from about 0.01% to about 0.8% by weight. Alternative suitable ranges for each preservative include from about 0.01% to about 0.7%, from about 0.01% to about 0.6%, from about 0.01% to about 0.5%, from about 0.01% to about 0.4%, from about 0.01% to about 0.3%, and from about 0.01% to about 0.2% by weight. Also suitable are preservative concentrations independently ranging from about 0.05% to about 0.7%, from about 0.05% to about 0.6%, from about 0.05% to about 0.5%, from about 0.05% to about 0.4%, from about 0.05% to about 0.3%, and from about 0.05% to about 0.2% by weight. Preferred concentration ranges for each preservative are from about 0.1% to about 0.7%, from about 0.1% to about 0.6%, from about 0.1% to about 0.5%, from about 0.1% to about 0.4%, from about 0.1% to about 0.3%, and from about 0.1% to about 0.2% by weight.

In certain embodiments, a third preservative, selected from benzyl alcohol, methyl paraben, and 4-chlorobutanol, is present, at a concentration from about 0.01% to about 0.8%, preferably from about 0.1% to about 0.8%, and more preferably from about 0.1% to about 0.4% by weight. Additional preservatives, such as EDTA, benzoate, sulfite, and the like, may optionally be present.

The propofol-dissolving oil used in the compositions of the invention may be any of the purified oils known in the pharmaceutical art to be suitable for injection. Suitable oils include, but are not limited to, triglycerides of medium chain C-8 to C-12 saturated and unsaturated pharmaceutically acceptable fatty acids, triglycerides of long chain C-14 to C-30 saturated and unsaturated pharmaceutically acceptable fatty acids, pharmaceutically acceptable vegetable oils, pharmaceutically acceptable fish oils, and mixtures thereof.

Preferred oils include soybean oil, safflower oil, cottonseed oil, corn oil, sunflower oil, arachis oil, castor oil, olive oil, and coconut oil, and combinations thereof. Soybean oil is particularly preferred.

The oil may be present in an amount from about 3% to about 20% by weight of the emulsion. Higher concentrations are regarded in the art as being less irritating upon injection, but practitioners may prefer to employ lower concentrations for patients at risk for hyperlipidemia. Compositions of the present invention preferably contain between about 5% and about 20% oil, and more preferably between about 10% and 20%, by weight.

The emulsions of the invention are stabilized by a surfactant, which may be any surfactant known in the art to be suitable for injection. Suitable surfactants include, but are not limited to, pharmaceutically acceptable non-ionic surfactants, pharmaceutically acceptable ionic surfactants, pharmaceutically acceptable phospholipids, pharmaceutically acceptable lecithins, and mixtures thereof. Preferred surfactants are egg lecithin, egg phosphatidylcholine, soy lecithin, soy phosphatidylcholine, and mixtures thereof. Egg yolk lecithin is particularly preferred.

The emulsions of the invention will preferably comprise a tonicity-modifying agent, so as to make the composition approximately isotonic with human blood. Any tonicity-altering agent known in the pharmaceutical arts may be employed, so long as it does not destabilize the emulsion. Non-ionic agents are preferred. Suitable agents include, but are not limited to, monosaccharides, disaccharides, trisaccharides, sugar alcohols, and mixtures thereof. Preferred agents are sucrose, dextrose, trehalose, mannitol, lactose, glycerol, and sorbitol, with mannitol being particularly preferred. Osmolalities of between 250 and 350 mOsmol/kg are preferred.

In the experiments described herein, an injectable propofol emulsion was prepared by combining propofol with a commercially-available, preservative-free 20% soybean oil emulsion stabilized with egg lecithin, which is marketed as an intravenous nutrient by Baxter Healthcare Inc. (Deerfield, Ill.) under the trade name INTRALIPID™. It contains 2.25% glycerin as a tonicity modifier, giving the emulsion an osmolality of approximately 350 mOsmol/kg.

Samples of the injectable emulsion were combined with two different preservatives, selected from benzyl alcohol, methyl paraben, 4-chlorobutanol, and trisodium citrate, at concentrations ranging from 0.1% to 0.4%. Each of these test samples was then inoculated with a fixed number of challenge organisms (*E. coli, S. aureus, P. aeruginosa*, and *C. albicans*) and incubated at room temperature for 24 hours. Samples were removed at 0, 6, 12, and 24 hours, and bacteria were filtered from the samples. The filters were then laid onto culture plates, incubated, and evaluated for microbial growth.

The results are shown in Table I. It can be seen from Table I that combinations of benzyl alcohol with methyl paraben and 4-chlorobutanol are effective, and that combinations of citrate with other preservatives are generally less effective.

It can also be seen from the Table that the combinations of 4-chlorobutanol and methyl paraben are noticeably more effective than any of the other tested permutations, including those that contain either 4-chlorobutanol or methyl paraben in combination with the other preservatives.

While the present invention is not limited to any particular theory of operation, applicants believe that the two preservatives are acting in concert with the inherent antimicrobial properties of propofol, which is present at low concentrations in the aqueous phase (see U.S. Pat. No. 7,097,849 and references therein.) It is theorized that microbial adaptations that might confer resistance to one or more of the antimicrobial agents are thwarted by the organisms' susceptibility to one or more of the additional agents.

TABLE I

| Sample | Organism | 0 hour | | 12 hour | | 24 hour | |
|---|---|---|---|---|---|---|---|
| | | Tube A | Tube B | Tube A | Tube B | Tube A | Tube B |
| | | | | CFU/mL | | | |
| Propofol Emulsion | S. aureus | 62 | 57 | 66 | 73 | 60 | 65 |
| Benzyl Alcohol 0.1% | P. aerug. | 29 | 15 | 8 | 5 | 0 | 0 |
| Methyl Paraben 0.1% | E. coli | 30 | 40 | 54 | 67 | 231 | 136 |
| | C. albicans | 33 | 31 | 40 | 27 | 111 | 85 |
| Propofol Emulsion | S. aureus | 57 | 61 | 66 | 75 | 49 | 49 |
| Benzyl Alcohol 0.3% | P. aerug. | 24 | 19 | 5 | 4 | 0 | 0 |
| Methyl Paraben 0.4% | E. coli | 38 | 33 | 30 | 31 | 31 | 29 |
| | C. albicans | 31 | 29 | 31 | 32 | 29 | 28 |
| Propofol Emulsion | S. aureus | 45 | 55 | 54 | 64 | 52 | 58 |
| Benzyl Alcohol 0.1% | P. aerug. | 20 | 27 | 0 | 0 | 0 | 0 |
| Trisodium Citrate 0.1% | E. coli | — | — | — | — | — | — |
| | C. albicans | 32 | 40 | 47 | 42 | TNTC* | TNTC |
| Positive Control | S. aureus | 66 | 74 | 40 | 64 | 47 | 45 |
| | P. aerug. | 16 | 21 | 10 | 9 | 17 | 22 |
| | E. coli | 47 | 43 | 65 | 32 | 260 | 277 |
| | C. albicans | 31 | 41 | 40 | 36 | 47 | 29 |
| Propofol Emulsion | S. aureus | 51 | 46 | 52 | 40 | 63 | 58 |
| Benzyl Alcohol 0.1% | P. aerug. | 19 | 25 | 12 | 16 | 2 | 2 |
| 4-Chlorobutanol 0.1% | E. coli | 35 | 34 | 22 | 23 | 91 | 83 |
| | C. albicans | 47 | 64 | 165 | 198 | TNTC | TNTC |
| Propofol Emulsion | S. aureus | 62 | 48 | 13 | 13 | 2 | 1 |
| Benzyl Alcohol 0.3% | P. aerug. | 33 | 25 | 0 | 0 | 0 | 0 |
| 4-Chlorobutanol 0.4% | E. coli | 55 | 60 | 23 | 40 | 41 | 39 |
| | C. albicans | 48 | 49 | 45 | 49 | 53 | 63 |
| Propofol Emulsion | S. aureus | 54 | 49 | 18 | 21 | 48 | 39 |
| Methyl Paraben 0.1% | P. aerug. | 32 | 42 | 0 | 1 | 0 | 0 |
| Trisodium Citrate 0.1% | E. coli | 48 | 63 | 13 | 8 | 195 | 191 |
| | C. albicans | 42 | 58 | 67 | 74 | 184 | 314 |
| Propofol Emulsion | S. aureus | 64 | 51 | 47 | 37 | 37 | 31 |
| Methyl Paraben 0.1% | P. aerug. | 41 | 33 | 8 | 4 | 0 | 0 |
| 4-Chlorobutanol 0.1% | E. coli | 53 | 63 | 29 | 63 | 30 | 43 |
| | C. albicans | 60 | 66 | 60 | 64 | 160 | 139 |
| Positive Control | S. aureus | 57 | 49 | 70 | 33 | 42 | 26 |
| | P. aerug. | 38 | 26 | 17 | 15 | 32 | 37 |
| | E. coli | 73 | 61 | 39 | 27 | 100 | 95 |
| | C. albicans | 41 | 55 | 56 | 49 | 83 | 88 |
| Propofol Emulsion | S. aureus | 55 | 50 | 46 | 60 | 52 | 37 |
| No Preservative | P. aerug. | 38 | 30 | 11 | 6 | 0 | 0 |
| | E. coli | 31 | 32 | 47 | 16 | 48 | 6 |
| | C. albicans | 50 | 43 | 41 | 66 | 202 | 277 |
| Propofol Emulsion | S. aureus | 49 | 57 | 4 | 6 | 1 | 1 |
| Methyl Paraben 0.4% | P. aerug. | 22 | 28 | 0 | 0 | 0 | 0 |
| 4-Chlorobutanol 0.4% | E. coli | 31 | 35 | 34 | 37 | 15 | 26 |
| | C. albicans | 41 | 48 | 36 | 33 | 25 | 32 |
| Propofol Emulsion | S. aureus | 42 | 48 | 82 | 42 | 44 | 41 |
| Trisodium Citrate 0.1% | P. aerug. | 35 | 36 | 5 | 5 | 0 | 0 |
| 4-Chlorobutanol 0.1% | E. coli | 34 | 32 | 76 | 60 | 137 | 167 |
| | C. albicans | 40 | 48 | 50 | 40 | TNTC | TNTC |
| Positive Control | S. aureus | 54 | 48 | 51 | 55 | 42 | 55 |
| | P. aerug. | 23 | 39 | 13 | 16 | 63 | 33 |
| | E. coli | 40 | 44 | 18 | 30 | 182 | 153 |
| | C. albicans | 42 | 47 | 51 | 40 | 50 | 52 |

TNTC*: too numerous to count

EXPERIMENTAL PROCEDURES

Propofol injectable 2% emulsion was prepared by blending propofol into an emulsion of 20% soybean oil, 1.2% egg yolk phospholipids, 2.25% glycerin, and water for injection, adjusted to pH 8.0 (INTRALIPID™ 20%, Baxter Healthcare, Deerfield Ill.) Test amounts of antimicrobial preservatives benzyl alcohol, trisodium citrate, methyl paraben and 4-chlorobutanol, in various combinations, were added.

Test and control formulations were challenged with 24-hr broth cultures of E. coli (ATCC 8739), S. aureus (ATCC 6538), and P. aeruginosa (ATCC 9027), and with a saline suspension of C. albicans (ATCC 10231). For each challenge, 10 ml of propofol injectable emulsion was placed into each of two sterile test tubes, and inoculated with the test organism at ca. 50 CFU/ml. Inoculated tubes were maintained at 20-25° C. throughout the challenge period. Inoculated positive controls (10 ml sterile phosphate buffer in identical test tubes) were run in parallel.

Two MICROFIL™ V brand membrane filters (0.45 micron, 47 mm hydrophilic mixed cellulose ester membranes, Millipore Inc., Billerica, Mass.) were pre-wet with sterile 0.1% peptone solution, and used in parallel with the two inoculated emulsions. Two identical filters were run with the inoculum check controls. At each time point (0, 6, 12, and 24 hours), 1.0 ml from each tube was filtered, each filter was rinsed twice with 100 ml sterile peptone. The filters were transferred to pre-poured plates of either tryptic soy agar (TSA) (for bacteria) or Sabouraud dextrose agar (SDA) (for C. albicans), and the plates were inverted and incubated. TSA plates were incubated at 30-35° C. for 2 days; SDA plates were incubated at 20-25° C. for 5 days. Colony-forming units were counted visually.

The results at 0, 12, and 24 hours, from three separate sets of experiments, are presented in Table I.

All documents, books, manuals, papers, patents, published patent applications, guides, abstracts and other reference materials cited herein, including GenBank Accession Numbers, are incorporated by reference in their entirety. While the foregoing specification teaches the principles of the present invention, with examples provided for the purpose of illustration, it will be appreciated by one skilled in the art from reading this disclosure that various changes in form and detail can be made without departing from the true scope of the invention.

We claim:

1. A sterile oil-in-water emulsion, comprising propofol in an amount from about 1% to about 8% by weight of the emulsion, a pharmaceutically acceptable propofol-dissolving oil in an amount from about 3% to about 15% by weight of the emulsion, and a pharmaceutically acceptable surfactant in an amount sufficient to stabilize the emulsion, wherein the ratio of oil to propofol is in the range of about 20:1 to about 1:1 by weight; further comprising a combination selected from the group consisting of
   combination (a): 4-chlorobutanol, in an amount from about 0.1% to about 0.8% by weight of the emulsion, and methylparaben, in an amount from about 0.1% to about 0.8% by weight of the emulsion; and
   combination (b): 4-chlorobutanol, in an amount from about 0.1% to about 0.8% by weight of the emulsion, and benzyl alcohol, in an amount from about 0.1% to about 0.8% by weight of the emulsion.

2. The emulsion of claim 1, wherein combination (a) comprises 4-chlorobutanol in an amount from about 0.1% to about 0.4% by weight of the emulsion, and methylparaben, in an amount from about 0.1% to about 0.4% by weight of the emulsion.

3. The emulsion of claim 1, wherein combination (b) comprises 4-chlorobutanol in an amount from about 0.1% to about 0.4% by weight of the emulsion, and benzyl alcohol, in an amount from about 0.1% to about 0.4% by weight of the emulsion.

4. The emulsion of claim 1, wherein combination (a) comprises 4-chlorobutanol in an amount from about 0.1% to about 0.2% by weight of the emulsion, and methylparaben, in an amount from about 0.1% to about 0.2% by weight of the emulsion.

5. The emulsion of claim 1, wherein combination (b) comprises 4-chlorobutanol in an amount from about 0.1% to about 0.2% by weight of the emulsion, and benzyl alcohol, in an amount from about 0.1% to about 0.2% by weight of the emulsion.

6. The emulsion of claim 1, wherein the propofol-dissolving oil is selected from the group consisting of triglycerides of medium chain C-8 to C-12 saturated and unsaturated pharmaceutically acceptable fatty acids, triglycerides of long chain C-14 to C-30 saturated and unsaturated pharmaceutically acceptable fatty acids, pharmaceutically acceptable vegetable oils, pharmaceutically acceptable fish oils, and mixtures thereof.

7. The emulsion of claim 6, wherein the oil is selected from the group consisting of soybean oil, safflower oil, cottonseed oil, corn oil, sunflower oil, arachis oil, castor oil, olive oil, and coconut oil, and combinations thereof.

8. The emulsion of claim 1, wherein the surfactant is selected from the group consisting of pharmaceutically acceptable non-ionic surfactants, pharmaceutically acceptable ionic surfactants, pharmaceutically acceptable phospholipids, pharmaceutically acceptable lecithins, and mixtures thereof.

9. The emulsion of claim 8, wherein the surfactant is selected from the group consisting of egg lecithin, egg phosphatidylcholine, soy lecithin, soy phosphatidylcholine, and mixtures thereof.

10. The emulsion of claim 1, further comprising a tonicity-modifying agent selected from the group consisting of monosaccharides, disaccharides, trisaccharides, sugar alcohols, and mixtures thereof.

11. The emulsion of claim 10, wherein the tonicity-modifying agent is selected from the group consisting of sucrose, dextrose, trehalose, mannitol, lactose, glycerol, and sorbitol.

12. The emulsion of claim 1, wherein combination (a) further comprises benzyl alcohol in an amount from about 0.1% to about 0.8% by weight.

13. The emulsion of claim 1, wherein combination (b) further comprises methyl paraben in an amount from about 0.1% to about 0.8% by weight.

14. The emulsion of claim 1, wherein the propofol-dissolving oil is selected from the group consisting of soybean oil, safflower oil, cottonseed oil, corn oil, sunflower oil, arachis oil, castor oil, olive oil, and coconut oil, and combinations thereof; the surfactant is selected from the group consisting of egg lecithin, egg phosphatidylcholine, soy lecithin, soy phosphatidylcholine, and mixtures thereof; and further comprising a tonicity-modifying agent selected from the group consisting of sucrose, dextrose, trehalose, mannitol, lactose, glycerol, and sorbitol.

15. The emulsion of claim 14, wherein combination (a) further comprises benzyl alcohol in an amount from about 0.1% to about 0.4% by weight.

16. The emulsion of claim 14, wherein combination (b) further comprises methyl paraben in an amount from about 0.1% to about 0.4% by weight.

* * * * *